(12) United States Patent
Nomura et al.

(10) Patent No.: US 6,706,533 B2
(45) Date of Patent: Mar. 16, 2004

(54) METHOD FOR DETECTING A CONCENTRATION OF A SOLUTION

(75) Inventors: Akio Nomura, Tokyo (JP); Tomoaki Iwao, Tokyo (JP)

(73) Assignee: Kanto Kagaku Kabushiki Kaisha, Tokyo (JP)

( * ) Notice: Subject to any disclaimer, the term of this patent is extended or adjusted under 35 U.S.C. 154(b) by 534 days.

(21) Appl. No.: 09/810,149

(22) Filed: Mar. 15, 2001

(65) Prior Publication Data

US 2001/0031501 A1 Oct. 18, 2001

(30) Foreign Application Priority Data

Mar. 15, 2000 (JP) .......................... 2000-072600

(51) Int. Cl.[7] .................... G01N 25/08; G01N 35/08; G01N 1/10; G01N 21/00; G01N 31/00; G01N 21/29; G05B 9/00
(52) U.S. Cl. .................... 436/150; 436/52; 436/179; 422/62; 422/82.05; 422/105
(58) Field of Search .................... 436/52, 150, 179; 422/62, 82.05, 105

(56) References Cited

U.S. PATENT DOCUMENTS

| | | | | |
|---|---|---|---|---|
| 4,822,744 A | * | 4/1989 | Bellows | 436/38 |
| 5,041,386 A | * | 8/1991 | Pierce et al. | 436/50 |
| 5,068,090 A | * | 11/1991 | Connolly | 422/82.02 |
| 5,137,831 A | * | 8/1992 | Gruteser | 436/52 |
| 5,149,661 A | * | 9/1992 | Gjerde et al. | 436/178 |
| 5,275,957 A | * | 1/1994 | Blades et al. | 436/133 |
| H1479 H | * | 9/1995 | Paulonis et al. | 422/82.02 |
| 5,725,754 A | * | 3/1998 | Belford | 205/789 |
| 5,843,602 A | | 12/1998 | Kotake | |
| 5,882,598 A | * | 3/1999 | Lindquist et al. | 422/82.02 |
| 6,004,515 A | * | 12/1999 | Parce et al. | 422/100 |
| 6,114,176 A | * | 9/2000 | Edgson et al. | 436/108 |
| 6,326,160 B1 | * | 12/2001 | Dunn et al. | 435/14 |
| 6,429,025 B1 | * | 8/2002 | Parce et al. | 436/514 |
| 6,451,613 B1 | * | 9/2002 | Blades et al. | 436/146 |
| 2003/0040122 A1 | * | 2/2003 | Blades et al. | 436/146 |
| 2003/0063997 A1 | * | 4/2003 | Fryer et al. | 422/3 |

FOREIGN PATENT DOCUMENTS

| | | |
|---|---|---|
| JP | 6-7910 | 2/1994 |
| JP | 6-29207 | 2/1994 |
| JP | 8-62852 | 3/1996 |

* cited by examiner

*Primary Examiner*—Jill Warden
*Assistant Examiner*—Brian R Gordon
(74) *Attorney, Agent, or Firm*—D. Peter Hochberg; Sean Mellino; Katherine R. Vieyra

(57) ABSTRACT

A concentration detection method and a concentration detection apparatus, and an agent diluting preparation apparatus capable of accurately estimating the concentration of a solution without the need of strict temperature control, and of estimating the concentration of the solution in real time, and further of cost reduction of diluting and preparing an agent and of simplification of diluting and preparing work are provided herein.

10 Claims, 4 Drawing Sheets

METHOD FOR DETECTING A CONCENTRATION OF A SOLUTION

BACKGROUND OF THE INVENTION

1. Field of the Invention

The present invention relates to a method and an apparatus for detecting the concentration of a desired substance in a solution as well as a diluting preparation apparatus for diluting and preparing a solid and a high concentration agent to a predetermined concentration.

2. Description of the Prior Art

Detection of the concentration of a specific substance in a solution is universally required in almost all industrial fields. Particularly, in industrial fields associated with semiconductors and liquid crystals, the ingredients and concentration of a solution must be frequently more strictly controlled and managed compared with those in other fields.

In fabrication steps for semiconductors for example, an alkali developing solution for use in development of a positive photoresist is a deciding factor to improve the resolution, dimensional accuracy, and stability, etc., of the photoresist, so that it is necessary to strictly control the ingredients and concentration of the solution while adjusting the positive photoresist used.

For a diluted hydrofluoric acid (an aqueous solution of hydrofluoric acid) for use in etching a silicon oxide film, etc., it is needed to accurately control the rate of etching or the amount of etching corresponding to the thickness of the silicon oxide film, etc. In order to achieve such a requirement it is needed to strictly control the concentration of the diluted hydrofluoric acid.

Japanese patents No. 2090366 (JP, 6-7910,B), No. 2751849 (cf. JP, 8-62852,A), No. 2670211(cf. JP, 6-29207, A; corresponding to U.S. Pat. No. 5,843,602) disclose a dilution apparatus for a developing stock solution equipped with control means for such concentration.

Hereupon, although agents for which strict concentration control is required are shipped to makers using such agents after makers supplying such agents dilute and adjust the concentrations of the agents to desired concentrations, recently there are increased cases in which the makers using such agents dilute and adjust high concentration agents to desired concentration ones.

These dilution apparatuses are classified to continuous ones disclosed in Japanese patents No. 2090366(JP, 6-7910, B) and No. 2751849, and to a batch one disclosed in Japanese Patent No. 2670211.

It is known that the electrical conductivity of a solution is varied depending upon the concentration and temperature of the solution. It is further known that in a wide temperature range and in a wide concentration range a relationship between concentration and electrical conductivity at a predetermined temperature and a relationship between electrical conductivity and temperature at a predetermined concentration do not satisfy a linear equation.

For this, in prior art measurements, it is assumed that after there are set temperature upon the measurement and concentration to be desired in the vicinity of the setting temperature and concentration the electrical conductivity is varied in terms of a linear equation of the concentration and it is further assumed that a change rate of the electrical conductivity upon the temperature being varied is unchanged without depending upon the concentration, and in the vicinity of the setting temperature and concentration, the concentration is estimated by measuring the electrical conductivity and the temperature.

Since the temperature of a solution is typically different from the setting temperature, the measurement for the solution is performed under the conditions where the temperature of the solution is kept at the setting temperature by passing the solution through a temperature controller.

In the continuous dilution apparatus, as disclosed in Japanese patents No. 2090366 (JP, 6-7910, B) and No. 2751849, there are set desired concentration and temperature, and the concentration of an agent is measured at all times while continuously supplying the agent or water, and the amount of supply of the agent or water is adjusted for dilution in response to the variations of the concentration.

Since the adjustment is performed in succession, it is desirable that the concentration measurement for agents is performed in real time, but the measurement of the concentration is retarded by the time that the solution passes through a temperature controller, so that excess and deficiency of an agent or water are likely to happen and hence greater concentration variations are likely to occur for a fluid taken out from a stirring tank into a storage tank.

The batch method is a method as disclosed in the Japanese Patent No. 2670211 wherein there is repeated an operation, where after an agent is diluted with water, the concentration of a diluted solution is measured to calculate the necessary amount of the agent and water and add them into a stirring tank until a solution that has a purposed concentration is obtained. Since in the present system, supply of the agent or water is not performed anew until the concentration is estimated, there can be taken at need the time for which the solution passes through the temperature controller, so that the concentration measurement is achieved more accurately than that of the continuous system. However, the batch system suffers from a difficulty that preparing time is prolonged because there is increased the time needed for the solution to pass through the temperature controller.

Further, the prior art measurement with a conductivity meter suffers from another difficulty that numerical values are inaccurate. Provided variations of the numerical values are large, the allowable concentration of an agent to be prepared must be more narrowed corresponding to those variations than that instructed by a user.

Makers using agents who require convenient concentration control desire that the aforementioned difficulties are solved as quickly as possible.

Although for accurately preparing an agent to a desired concentration it is essential to accurately detect the concentration of the agent, there is a relationship expressed by a linear equation in a predetermined temperature range and at a predetermined temperature both defined by the agent between the concentration of the agent and the electrical conductivity of the solution, so that it is conventionally general that for an electrical conductivity meter used for the control of the concentration there is grasped a relationship between the electrical conductivity of the solution at a predetermined temperature and the concentration of an agent and a relationship between the electrical conductivity of the solution at a certain temperature and the temperature, and that the concentration of the agent is calculated upon measuring the electrical conductivity of the solution, based upon a measured value.

More specifically, there is estimated by an experiment a linear equation $Dt=a'C+b'$ ($Dt$ indicates an electrical conductivity, $C$ concentration, and $a'$ and $b'$ indicate constants.) representative of a relationship between the electrical conductivity of a solution and the concentration of an agent at a certain temperature (setting temperature t). Then, it is assumed that the electrical conductivity becomes higher by d every time the measurement temperature of the electrical conductivity becomes higher by 1 degree than the setting temperature t, and the d is estimated by the experiment. Accordingly, provided the electrical conductivity when the temperature of a solution is T is DT, the electrical conductivity Dt of the solution at the setting temperature t is represented by a formula Dt=Dt−d(T−t). In contrast, since Dt=a'C+b', DT−d(T−t)=a'C+b', and solving the equation with respect to C, C=(DT−d(T−t)−b')/a'. Even when the measurement temperature of the electrical conductivity is shifted from the setting temperature t, temperature compensation is achieved using the foregoing last equation, and hence the concentration is calculated from the electrical conductivity.

However, since the prior art presupposes the assumption that in a predetermined temperature and concentration region determined by the agent the electrical conductivity becomes higher by d every time the measurement temperature of the electrical conductivity becomes higher by 1 degree, accurate concentration of the solution can be calculated provided the temperature of the solution is the same as the setting temperature, but when the temperature of the solution is shifted from a predetermined measurement temperature, there is produced an error between actual concentration and calculated concentration. Thus, the prior art suffers from a difficulty that it is difficult to grasp the concentration with accuracy tolerable against the conditions where strict concentration control management is needed.

The prior art further suffers from a difficulty associated with the foregoing difficulties, as mentioned in the foregoing Japanese patent No. 2090366(JP, 6-7910, B), that the electrical conductivity is needed to be measured in the state where the temperature of a solution is kept at the setting temperature with the aid of a temperature controller. For this, there is required a heat source for a temperature keeping apparatus and the like and installation investment for the temperature controller, resulting in the high cost of dilution preparing of an agent and complicated work. There is further another difficulty that when the concentration measurement is continuously performed with the aid of a temperature controller, there is the need of keeping the temperature at the set one, so that the measurement is retarded by the time required for the solution to pass through the temperature controller also as disclosed in Japanese patents No. 2090366 (JP, 6-7910) and No. 2751849.

SUMMARY OF THE INVENTION

It is therefore an object of the present invention to provide a method and an apparatus for detecting the concentration of a solution and an apparatus for diluting and preparing an agent wherein the concentration of a solution can be obtained accurately and reproducibly even without strict temperature control, and the concentration can be obtained in a real time, and further the cost of dilution and preparing of an agent can be reduced and diluting and preparing work can be simplified.

The present inventors have found solving means to complete the present invention as a result of the pursuit of our studies to solve the aforementioned difficulties.

The present invention relates to a method for detecting the concentration of a solution comprising a step for measuring the electrical conductivity and temperature of the solution and a step for calculating the concentration of a desired substance in the solution from the foregoing electrical conductivity and the foregoing temperature based upon the following equation:

$$C=(D-aT-b)/(AT+B) \quad (1)$$

wherein C is the concentration of a desired substance, D is the electrical conductivity of a solution at temperature T, T is the temperature of the solution, and A, B, a, and b represent a constant, respectively.

The present invention further relates to the aforementioned method for detecting the concentration of a solution wherein the constants A, B, a, b in the equation are values obtained by measuring the electrical conductivity of the solution at the plurality of the temperatures for each solution containing the same desired substance with the plurality of the concentrations while applying the least squares method to a measured result.

The present invention further relates to the aforementioned method wherein the constants A, B, a, b are values obtained by a method comprising a first step for measuring the electrical conductivity at a plurality of temperatures for each solution containing the same agent with a plurality of the concentrations, a second step for deriving a linear equation by the least squares method for a relationship between the temperature and the electrical conductivity with each concentration, a third step for substituting the plurality of the temperatures for each of the foregoing linear equation and calculating the electrical conductivity at each temperature, a fourth step for deriving a linear equation with the least squares method with respect to a relationship at each temperature in the third step, and a fifth step for deriving linear equations w=AT+B and z=aT+b with temperature for each of the inclination w and the concept of each linear equation obtained in the fourth step.

The present invention further relates to the foregoing method for detecting the concentration of a solution where in the plurality of the temperatures are included within a temperature range of ±5 degrees of the desired temperature.

The present invention still further relates to the aforementioned method for detecting the concentration of a solution wherein the plurality of the temperatures are included within a temperature range of ±10 degrees of the desired temperature.

The present invention furthermore relates to a method for detecting the concentration of a solution where in the solution is an aqueous solution.

The present invention still furthermore relates to the aforementioned method for detecting the concentration of a solution wherein the solution contains only one kind of a solute.

The present invention further relates to a method for diluting and preparing an agent to a desired concentration utilizing the aforementioned method for detecting the concentration of a solution.

The present invention relates to the aforementioned method for diluting and preparing an agent comprising a first step wherein the agent is mixed with water into an aqueous solution, a second step wherein the concentration of the agent in the aqueous solution is detected, and a third step wherein an agent or water is added to the aqueous solution to adjust the concentration of the agent to a desired concentration.

The present invention further relates to the aforementioned method for diluting and preparing an agent wherein at least the second step and the third step are controlled with a computer program.

The present invention still further relates to a concentration detecting apparatus comprising electric conductivity measuring means and arithmetic operation means for detecting the concentration of a desired substance in a solution by the arithmetic operation means based upon the electric conductivity of the solution measured by the electric conductivity measuring means, the arithmetic operation means calculating the following equation:

$$C=(D-aT-b)/(AT+B) \quad (1)$$

wherein C designates the concentration of a desired substance, D is electric conductivity of the solution upon temperature T, T is the temperature of the solution, and A, B. a, and b each denote a constant.

The present invention yet still further relates to the concentration detecting apparatus wherein the constants A, B, a, b in the equation (1) are values by measuring for each of the solutions containing the same desired substance at a plurality of concentrations, the electric conductivities at a plurality of temperatures and by applying the least square method thereto.

The present invention further relates to the concentration detecting apparatus wherein the constants A, B, a, b are values calculated for solutions containing the same agent with a plurality of concentrations by a method comprising: a first step for measuring electric conductivities at a plurality of temperatures, a second step for deriving a linear equation with the method of least square for a relationship between the temperature and the electric conductivities at the respective concentrations, a third step for substituting the aforementioned plurality of temperatures for each of the linear equations to calculate the electric conductivity at each temperature, a fourth step for deriving a linear equation by the least squares method with respect to a relationship between the electric conductivity and the concentration at each temperature in the third step, and a fifth step for deriving linear equations w=AT+B and z=aT+b with respect to temperature for each inclination w and an intercept z of each linear equation obtained in the fourth step.

The present invention relates to the aforementioned concentration detecting apparatus wherein the plurality of temperatures are included within a temperature range of 5± degrees.

The present invention further relates to the aforementioned apparatus wherein the plurality of temperatures are included within a desired temperature range of ±10 degrees.

The present invention relates to the aforementioned concentration detecting apparatus wherein a solution to be measured is an aqueous solution.

The present invention further relates to the aforementioned concentration detecting apparatus wherein a solution to be measured involves only one kind of solute.

The present inventors have found the following two facts as a result of thorough investigation on why variations of numerical values are large: that (1) air bubbles remaining in a measuring chamber sharply influences measured values, (2) there is left behind a solution used at the previous time of measurement in the measuring chamber depending upon the configuration of the inside of the measuring chamber, which solution is then mixed with a fluid flowing into next time to change the concentration of the solution. More specifically, the configuration of the measuring chamber maybe one having an outlet for aqueous solution at the head of the chamber and is desirable for the configuration which prevents any fluid from remaining in the measuring chamber The configuration is preferable which is continuously reduced in size toward the outlet for aqueous solution for example, but it is not limited thereto.

The present invention accordingly also relates to the aforementioned concentration detecting apparatus wherein electric conductivity measuring means includes a measuring chamber provided with an inlet for aqueous solution and a flow outlet at the head, and a horizontal cross sectional area of the measuring chamber is continuously reduced toward the outlet for aqueous solution.

A measuring rod is disposed in the measuring chamber, which rod has a through-hole therethrough. Provided that air bubbles flow into the through-hole, it influences measured values if it is not removed quickly. To improve such a situation, the present inventors have found that a water flow may be formed in the direction of the through-hole in the measuring chamber.

A further one inlet for aqueous solution is for example preferably provided in the vicinity of an intersection between an extension line of the through-hole and a wall surface of the measuring chamber, but the present invention is not limited thereto.

The present invention accordingly further relates to the aforementioned concentration detection apparatus wherein the measuring chamber includes a measuring rod disposed there in having a through-hole therethrough, and further, another inlet for aqueous solution is provided in the vicinity of an intersection between an extension line of the through-hole and a wall surface of the measuring chamber.

The present invention further relates to the aforementioned agent diluting preparation apparatus equipped with the aforementioned concentration detection apparatus for diluting and preparing an agent to a desired concentration by mixing the agent with water.

The present invention still further relates to the aforementioned agent diluting and preparing apparatus including a diluting and preparing tank, mixing means for mixing an agent with water into an aqueous solution, and concentration adjusting means for adjusting the concentration of the agent to a desired one by adding an agent or water into an aqueous solution based upon detected concentration.

The present invention furthermore relates to the aforementioned agent diluting and preparing apparatus wherein at least the concentration detection apparatus and the concentration adjusting means are controlled with a computer program.

The present invention further relates to the aforementioned agent diluting and preparing apparatus wherein upon measuring the electric conductivity and temperature part of the aqueous solution is temporarily sent from the diluting and preparing tank to the electric conductivity measuring means of the concentration detecting apparatus, and the electric conductivity measuring means includes a measuring chamber having an inlet for aqueous solution and an outlet for aqueous solution at the head thereof, and further a horizontal cross sectional area of the measuring chamber is continuously reduced toward the outlet for aqueous solution.

The present invention further relates to the aforementioned agent diluting and preparing apparatus wherein the measuring chamber includes a measuring rod disposed in the measuring chamber, and the measuring rod has a through-hole, and further the measuring rod further includes another inlet for aqueous solution in the vicinity of an intersection between an extension line of the through-hole and a wall surface of the measuring chamber.

The above and other objects, advantages and features of the present invention will be more apparent from the following description taken in conjunction with the accompanying drawings.

BRIEF DESCRIPTION OF THE DRAWINGS

FIG. 7($b$) is a schematic cross-sectional view illustrating another example (b) of conductivity measuring means.

DETAILED DESCRIPTION OF THE PREFERRED EMBODIMENTS

Figure 1:
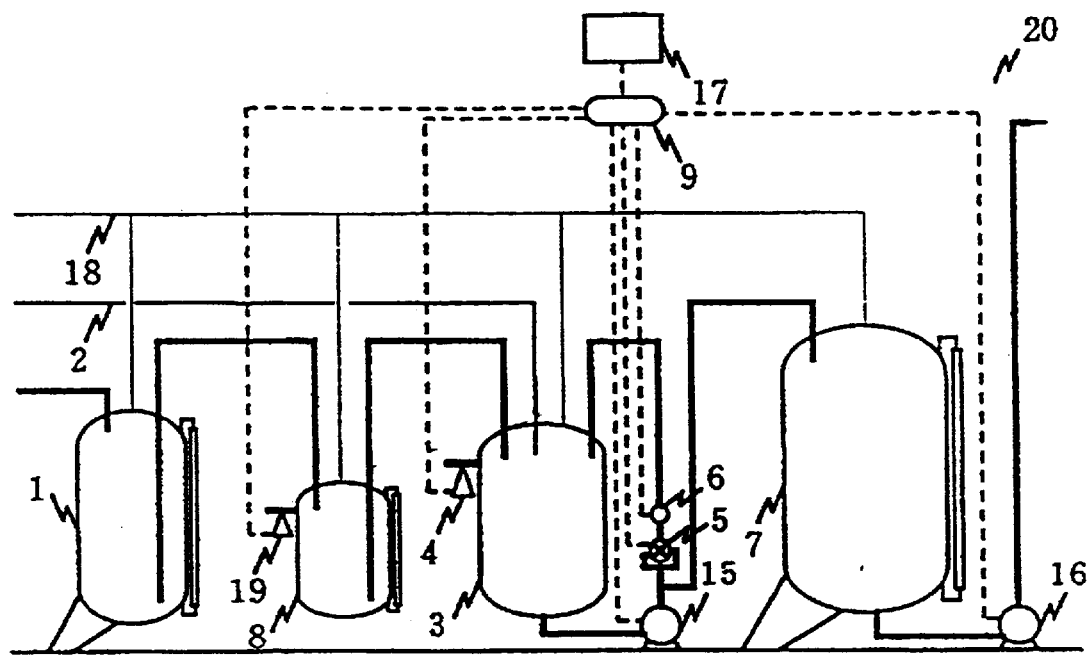
FIG. 1 is a schematic exemplarily illustrating one example of a diluting preparation apparatus of the present invention.

In the present invention, the concentration of a desired substance in a solution is estimated through an equation (1) $C=(D-aT-b)/(AT+B)$, wherein C denotes the concentration of a desired substance, D is the electric conductivity of the solution at temperature T, T is the temperature of the solution, and A, B, a, and b denote constants, based on the measured values of the electric conductivity of the solution.

The relationship between the electric conductivity D and the concentration C of a solution at a predetermined temperature can be approximated with a relationship represented by a linear equation $D=wC+z$ in a narrow concentration range. The inclination w and intercept of the approximate linear equation, however, change as the temperature of the solution changes. The present invention is based upon new information that the relationship between the inclination w and intercept z of the approximate linear equation representing the relationship among the electric conductivity and the concentration C and the temperature T can be represented by a linear function of temperature T in a narrow temperature range within $\Delta T$ 20 degree. More specifically, the inclination of the aforementioned linear equation $D=wC+z$ is represented by $\Delta T+B$, and the intercept z is represented by $aT+b$. The electric conductivity D of a solution is thus represented by $(AT+B)C+(aT+b)$, and the aforementioned equation (1) is derived by solving the expression of D with respect to the concentration C.

More specifically, in the present invention, it is possible to accurately calculate the concentration of the solution by calculating the concentration from the electric conductivity using the equation (1) that is the relationship between temperature and the electric conductivity and concentration of the solution without the need of the temperature of the solution bringing to a predetermined one upon measuring the electric conductivity. It is contemplated to be rare that variations of the temperature of the solution the electric conductivity being actually measured exceeds ±10 degrees. Accordingly, provided that the electric conductivity can be accurately measured within the foregoing temperature range, the measurement is sufficient for the detection of the concentration. Further, considering the fact that a variation range of the temperature of a solution for which the electric conductivity can be accurately measured in the prior art concentration detecting method falls within ±5 degrees, the concentration can be accurately detected even if the temperature of the solution is varied with in $\Delta T=20$ degrees. Such availability of the present invention is clear.

The constants A, B, a, and b of the equation (1) can be estimated as follows, for example: for solutions having a plurality of concentrations and including the same kind of an agent electric conductivities thereof are first measured at a plurality of temperatures. Then, a linear equation $$D=wC+z \qquad (2)$$

is derived from the relationship between the temperature and electric conductivity of the solution with each concentration using the least squares method. Then, the inclination w of the foregoing linear equation (2) is estimated as an equation representing a linear function with respect to temperature $$w=AT+B \qquad (3)$$

from the relationship between temperature at each concentration and the electric conductivity with the aid of the least squares method, and the intercept z of the foregoing linear equation (2) is derived as an equation $$z=aT+b \qquad (4)$$

represented by a linear function with respect to temperature, to previously estimate the constants A, B, a, and b.

The constants A, B, a, and b in the equation (1) can be also estimated even with the following method. First, a solution containing an agent of the same kind with a plurality of kinds of the concentrations electric conductivities are measured at a plurality of temperatures. Measured numerical values are substituted for the following matrix.

$$\begin{pmatrix} \sum DT^2C \\ \sum DC \\ \sum DT \\ \sum D \end{pmatrix} = \begin{pmatrix} \sum T^2C & \sum TC & \sum T^2C & \sum TC \\ \sum TC^2 & \sum C^2 & \sum TC & \sum C \\ \sum T^2C & \sum TC & \sum T^2 & \sum T \\ \sum TC & \sum C & \sum T & \sum \end{pmatrix} \begin{pmatrix} A \\ B \\ a \\ b \end{pmatrix} \qquad \text{(Equation 1)}$$

The constants are determined by solving the matrix.

Herein, the temperatures of the plurality of kinds are assumed to be ones of 5 kinds or more, more preferably of 10 kinds or more with temperature differences there among $\Delta T=20$ degrees, preferably $\Delta T=10$ degrees. The values of the foregoing constants A, B, a, and b should be estimated taking the desired temperature of an agent solution upon measuring the concentration and electric conductivity of an agent solution to be adjusted. The values of the constants A, B, a, and b are also varied even with solvents of agent solutions and kinds of agents.

The plurality of temperatures used for calculating the constants A, B, a, and b are preferably included within a temperature range of a desired temperature ±5 degrees, and more preferably included within a temperature range of the desired temperature ±10 degrees. The solution is an aqueous solution, which preferably includes a solute of only one kind. The present invention is particularly useful upon detecting concentrations of agents requiring strict concentration control. For such agents there are known for example tetramethylammonium hydroxide (TMAH), sodium hydroxide, potassium hydroxide, sodium carbonate, hydrofluoric acid, hydrochloric acid, etc.

EXAMPLE

The invention will be explained using the following examples in more detail without being limited to these examples.

Example 1

FIG. 1 schematically illustrates an embodiment of a diluting preparation apparatus according to the present invention. The diluting preparation apparatus 20 comprises a stock solution storage tank 1 which stores a raw material of an agent, a pure water supplying pipe 2 from which pure water is supplied, a diluting preparation tank 3, a load cell 4, an electric conductivity meter 5, a resistance temperature sensor (thermometer) 6, a supply tank 7 in which a diluting preparation agent solution is stored, and pipes by which these each devices are connected, and electrical instruments.

A stock solution of an agent for electronic industries is stored in the raw material storage tank 1, and is supplied into a measuring tank 8 following an instrument reading of the load cell 4. The stock solution of an agent for electronic industries is supplied into the measuring tank 8 up to a desired weight by the load cell 19, and then the stock solution is supplied into the diluting preparation tank 3 up to a desired weight by the load cell 4. Thereafter, pure water is supplied into the diluting preparation tank 3 up to a desired weight by the load cell 4. Stirring by nitrogen bubbling or pump circulation is performed until the agent to be diluted and prepared is mixed sufficiently, and then an electronic conductivity and temperature are measured with the electronic conductivity meter 5 and the resistance temperature sensor 6. The electric conductivity and the temperature are outputted to a system control instrument 9, and are substituted for the following equation (1) inputted previously into the system control instrument 9 to derive the concentration of the mixed solution. The equation (1) is $C=(D-aT-b)/(AT+B)$, wherein C is a concentration of a desired substance, D is an electrical conductivity of a solution at temperature T, T is a temperature of the solution, and A, B, a, and b denote constants.

The equation (1): $C=(D-aT-b)/(AT+B)$, wherein C is a concentration of a desired substance, D is an electrical conductivity of a solution at temperature T, T is a temperature of the solution, and A, B, a, and b denote constants, has been previously inputted into the system control instrument 9, and the constants A, B, a, and b are, for example, previously determined as follows.

Figure 2:
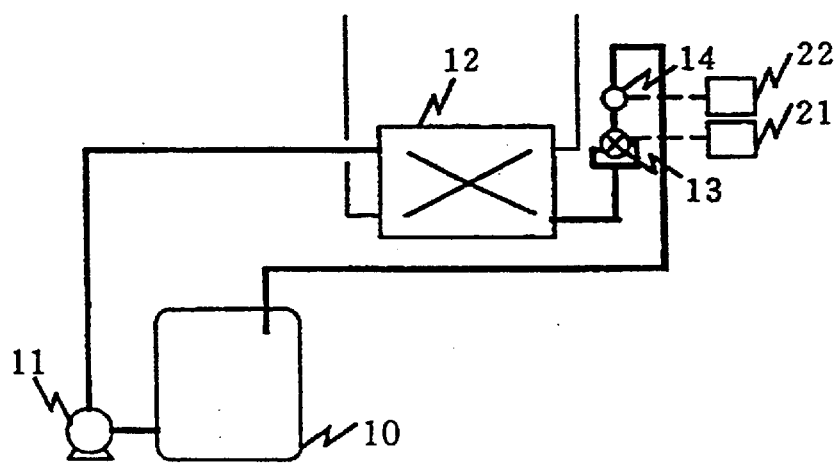
FIG. 2 is a schematic exemplarily illustrating one example of an experimental apparatus used for investigating a relationship among the concentration, temperature, and electric conductivity of a solution.

For example, a relationship among the concentration, temperature, and electric conductivity of a solution is investigated employing such an experimental apparatus illustrated in FIG. 2. As an example, the case of investigation of a relationship between the concentration, temperature, and electric conductivity of an aqueous solution of TMAH widely employed as an alkaline developing solution for use for developing positive-type photoresist in a step for producing a semiconductor. This example is the case wherein the constants A, B, a, and b are determined on the assumption that an aqueous solution of 2.380% by mass of TMAH is prepared at temperature of 20 to 30° C.

Figure 3:
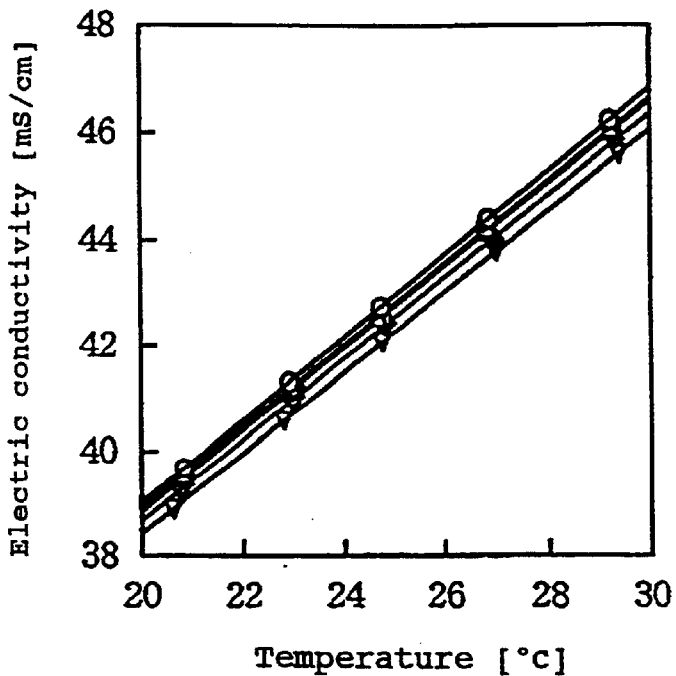
FIG. 3 is a graphical representation illustrating a relationship between the temperature and concentration of an aqueous solution of TMAH at each concentration.

First in general, an aqueous solution of 2.390% by mass of TMAH is introduced into a container 10. A pump 11 is operated to circulate the aqueous solution of TMAH through a temperature adjusting unit 12, an electric conductivity meter 13, and a resistance temperature sensor 14 at a flow rate of about 2.5 liters per minute. Setting temperature of the temperature adjusting unit 12 is changed to 20, 22.5, 25, 27.5, 30° C., and the electrical conductivity of the aqueous solution of TMAH at each temperature is measured with the electrical conductivity meter 13. As to the aqueous solutions of TMAH with the concentration of 2.385, 2.380, 2.375, 2.370% by mass, electrical conductivities at the foregoing temperatures are measured. As an example performed herein, electrical conductivities were measured using the aqueous solution of TMAH of 2.392, 2.382, 2.379, 2.367, and 2.370% by mass. FIG. 3 illustrates a relationship between the temperature and electric conductivity of the aqueous solution of TMAH at each concentration.

Figure 4:
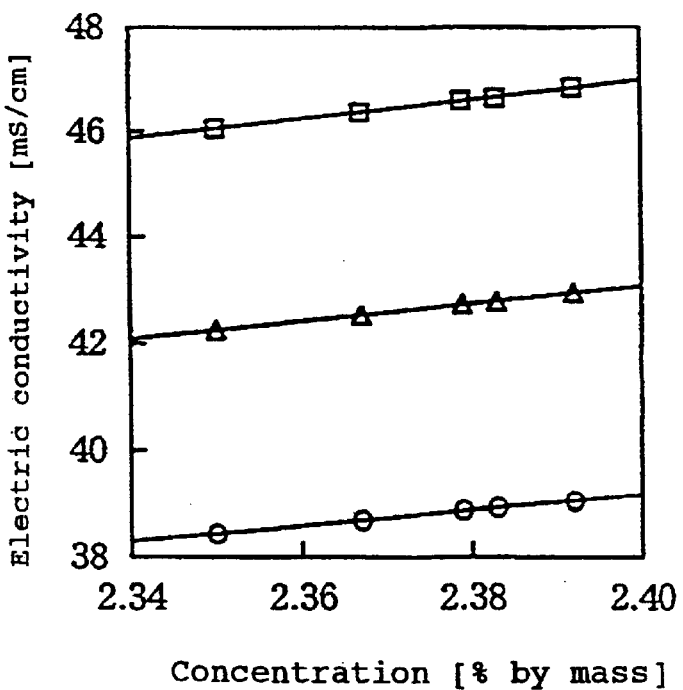
FIG. 4 is a graphical representation illustrating a relationship between the concentration and electric conductivity of an aqueous solution of TMAH at each temperature.

Then, the constants A, B, a, b are estimated using the least squares method. Although they can be estimated in one step using the least squares method, a successive method for estimating them in succession is disclosed herein. An approximate linear equation is derived for a relationship between the temperature and electric conductivity of the aqueous solution of TMAH at each concentration. An approximate linear equation at each concentration is listed in Table 1. It is found from the change of the concentration from Table 1 that the inclination and intercept of the linear equation are varied. Then, 20, 25, 30° C. are substituted for T (temperature) in each approximate linear equation in Table 1, and the electric conductivity at each temperature is estimated. FIG. 4 illustrates a relationship between the concentration and electric conductivity at each temperature. Further, Table 1 illustrates the electric conductivity at each temperature.

TABLE 1

| Concentration [% by mass] | Equation of electric conductivity-temperature | Electric conductivity at 20° C. [mS/cm] | Electric conductivity at 25° C. [mS/cm] | Electric conductivity at 30° C. [mS/cm] |
| --- | --- | --- | --- | --- |
| 2.392 | D = 0.7808T + 23.42 | 39.03 | 42.94 | 46.84 |
| 2.383 | D = 0.7744T + 23.43 | 38.92 | 42.79 | 46.66 |
| 2.379 | D = 0.7747T + 23.36 | 38.85 | 42.72 | 46.60 |
| 2.367 | D = 0.7678T + 23.33 | 38.68 | 42.52 | 46.36 |
| 2.350 | D = 0.7619T + 23.20 | 38.44 | 42.25 | 46.06 |

Then, using the least squares method, the approximate linear equation with respect to the relationship between the concentration and electric conductivity of the aqueous solution of TMAH at each temperature is derived. Table 2 shows the approximate linear equation at each temperature.

TABLE 2

| Temperature [° C.] | Equation of electric conductivity-concentration | Distinction of inclinations | Distinction of intercept |
|---|---|---|---|
| 20 | D = 18.62C + 2.293 | 2.200 | −1.361 |
| 25 | D = 16.42C + 3.654 | 2.200 | −1.361 |
| 30 | D = 14.22C + 5.015 | | |

It is found from Table 2 that distinctions among inclinations and distinctions among intercepts among the approximate lines are equal to each other. Therefore, the inclination w and the intercept z can be expressed as a linear function depending upon temperature T. Hereby, A, B, a, b in w=AT+B and z=aT+b are determined, and hence the respective constants in the equation (1): $C=(D-aT-b)/(AT+B)$, are determined.

TABLE 3

| Inclination w | W = 0.4398T + 5.427 |
|---|---|
| Intercept z | Z = −0.2722T + 10.46 |

For example, it runs as follows to dilute and prepare an aqueous solution of 2.380% by mass of TMAH at temperature of 20 to 30° C. using the equation obtained in the aforementioned step: $C=(D+0.2723T-10.46)/(0.4398T+5.427)$.

First, in the diluting preparation apparatus illustrated in FIG. 1, an agent and water are mixed and stirred in the diluting preparation tank into a uniform aqueous solution. Then, the concentration of the agent in the aqueous solution is detected. The concentration, which derived from the aforementioned equation substituted with the temperature and electric conductivity of the diluted and prepared aqueous solution, is outputted to the system control instrument 9 as the concentration adjusting means controlled by a computer program. And the outputted concentration is compared with a previously set desired value(2.380% by mass) and an allowable error range(±0.005% by mass). If the outputted concentration falls within an allowable error range with respect to the desired value, then the aqueous solution is sent to the supply tank 7. In contrast, if the concentration of the aqueous solution is less than the desired value involving the allowable error range, then the stock solution of the agent is supplied, while if it exceeds the desired value involving the allowable error range, then the solution is adjusted by supplying pure water. As to the adjusted aqueous solution, the foregoing step is repeated until the concentration of the solution falls within the desired value involving the allowable error range. Even though in the diluting and preparing step for the stock solution of the agent the temperature of the agent solution is varied in the range of 20 to 30° C., the concentration of a resulting aqueous solution of TMAH is 2.380% by mass (measured by a neutralization titration method).

The aforementioned step including the mixing and stirring of an agent and water, the measurement of an electric conductivity, calculation of concentration, comparison with a desired value, and supplement of water or an agent stock solution are preferably controlled with a computer program.

Further, for the detection of the concentration of the diluted and prepared agent, a method is preferably employed in which a part of the agent solution from the diluting preparation tank 3 is temporarily conveyed to the electric conductivity meter 5 and the resistance temperature sensor 6, the electric conductivity and temperature are measured, and then the agent solution is returned to the diluting preparation tank 3. In this case, the electric conductivity meter 5 is adapted, as illustrated in FIGS. 7(a) and 7(b), such that it includes an inlet for an aqueous solution 30 and an outlet for an aqueous solution 31, and has a measuring rod 33 disposed in the measuring chamber 32 constructed in liquid tight, whereby the measuring rod 33 measures the electric conductivity of the aqueous solution flowing from the inlet for an aqueous solution 30 to the outlet for aqueous solution 31.

Figure 7A:
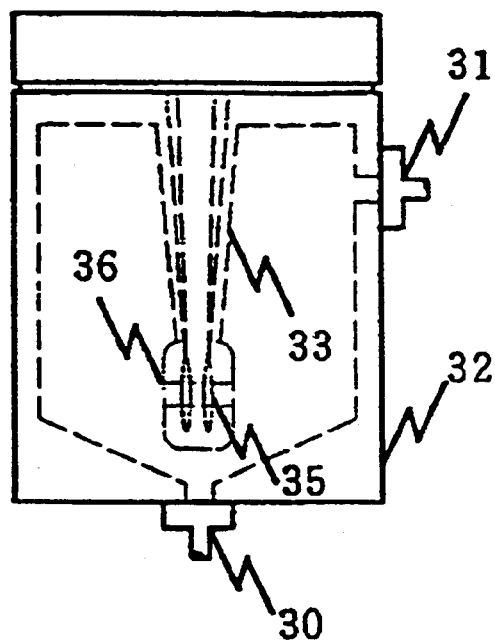
FIG. 7($a$) is a schematic cross-sectional view illustrating one example (a) of electric conductivity measuring means.
Figure 7B:
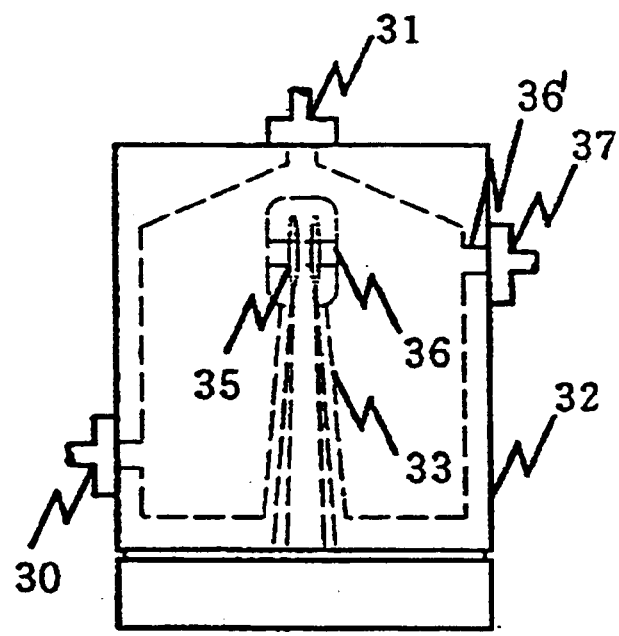

However, trouble might frequently occur when the electric conductivity meter 5 having the arrangement illustrated in FIG. 7(a) is employed, in that air bubbles stay along a ceiling of the measuring chamber 32 to cause variations of measured values of the electric conductivity. Further, there might occur an occasion where a solution flowing into the measuring chamber upon previous measurement stays in the measuring chamber and hence is mixed with a fluid flowing in anew to cause decrease of accuracy of measured values. To eliminate these troubles, the outlet for aqueous solution 31 is disposed on a head of the measuring chamber 32, as illustrated in FIG. 7(b), and, in the vicinity of the outlet for aqueous solution 31, a horizontal cross sectional area of the measuring chamber 32 is continuously reduced as it goes toward the outlet for aqueous solution 31. Hereby, the use of an electric conductivity meter in which air bubbles along the ceiling are prevented from staying is preferable in view of reduction of variations of measured values. In this situation, the measuring rod 32 is preferably protruded from a side wall or a bottom surface of the measuring chamber 32 from the view point of effectively preventing the staying of the air bubbles.

Further, the measuring rod 33 has a through-hole 36 equipped with two electrodes 35 and measures therewith the electric conductivity of an aqueous solution upon both electrodes 35 being filled with the aqueous solution passing through the inside of the through-hole 36. Accordingly, provided air bubbles stay in the through-hole 36, the electric conductivity is prevented from being accurately measured. In order to effectively remove air bubbles in the through-hole 36, there may be preferably provided further another inlet for aqueous solution 37 in the vicinity of an intersection between an extension line of the through-hole 36' and a wall surface of the measuring chamber 32 as illustrated in FIG. 7(b).

An upper space of the stock solution storage tank 1, measuring tank 8, diluting preparation tank 3, and supply tank 7 may be preferably encapsulated with inactive gas in order to prevent carbon dioxide gas from being sucked therethrough. Further, the diluted and prepared agent stored in the supply tank 7 may be supplied to a user side through a filter 15 by operating the pump 14 following a request signal on the user side.

Example 2

The constants A, B, a, and b of the equation (1): $C=(D-aT-b)/(AT+B)$, in the case where a stock solution of hydrofluoric acid is diluted to prepare an aqueous solution of 1.0% by mass of hydrofluoric acid, are determined with the same procedure as the example 1. It is supposed, as in the example 1, that the stock solution of hydrofluoric acid is adjusted at the temperature of 20 to 30° C.

Figure 5:
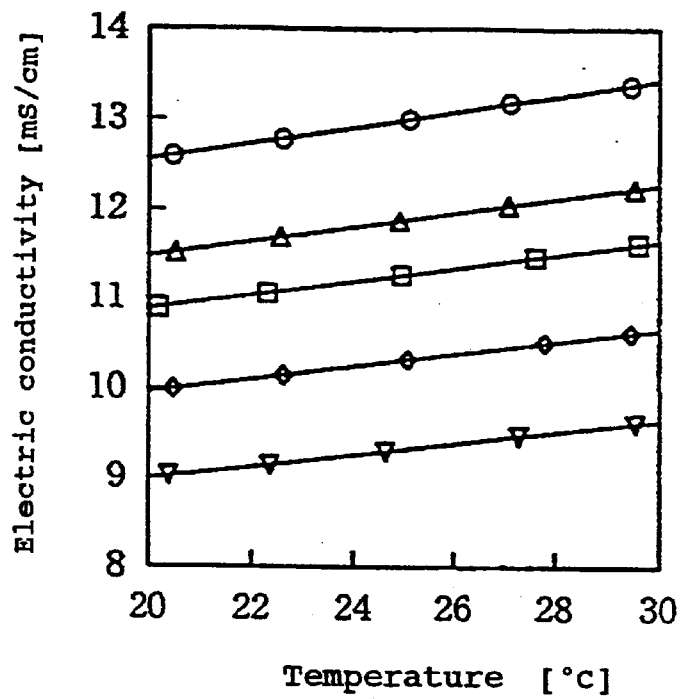
FIG. 5 is a graphical representation illustrating a relationship between the temperature and electric conductivity of an aqueous solution of hydrofluoric acid at each concentration.

As in the example 1, a relationship among the concentration, temperature, and electric conductivity of a solution is investigated using an experimental apparatus illustrated in FIG. 2. As to the aqueous solution of hydrofluoric acid with the concentration of any of 1.2, 1.1, 1.0, 0.9, and 0.8% by mass, the electric conductivity of the aqueous solution at each temperature is measured with the electric conductivity meter 13 by changing the setting temperature to 20, 22.5, 25, 27.5, 30 while circulating the solution through the temperature adjusting unit 2, electric conductivity meter 13, and resistance temperature sensor 14. As an example executed herein, a measurement using an aqueous solution of hydrofluoric acid with the concentration of any of 1.189, 1.073, 1.009, 0.910, and 0.806% by mass is performed. FIG. 5 illustrates a relationship between the temperature and electric conductivity of the aqueous solution of hydrofluoric acid at each concentration.

Figure 6:
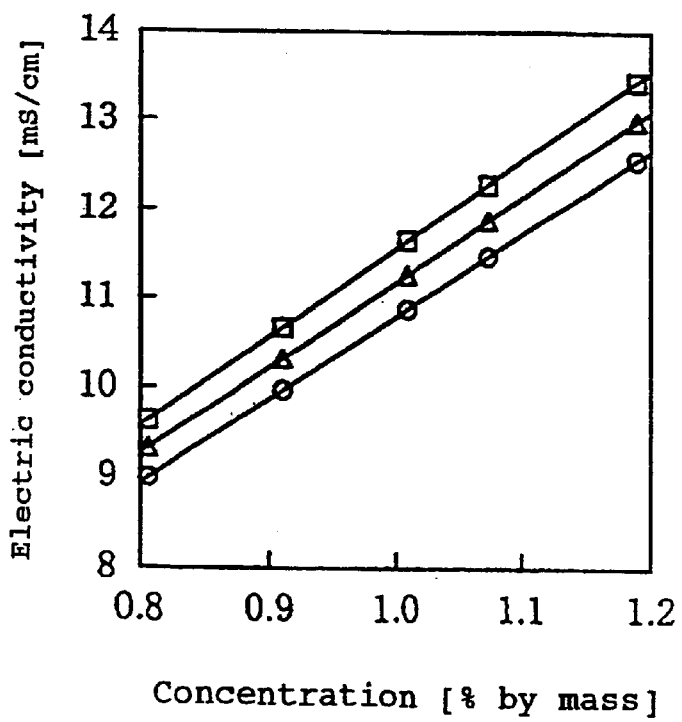
FIG. 6 is a graphical representation illustrating the concentration and electric conductivity of an aqueous solution of hydrofluoric acid at each temperature.

Then, an approximate linear equation is derived for a relationship between the temperature and electric conductivity of the aqueous solution of hydrofluoric acid at each concentration using the least squares method. Table 4 illustrates an approximate linear equation at each concentration. It is found from a concentration change in Table 4 that the inclination and intercept of the linear equation are varied. Then, each of 20, 25 and 30° C. is substituted for T of each approximate linear equation in Table 4 to estimate the electric conductivity at each temperature. FIG. 6 illustrates a relationship between the concentration and electric conductivity at each temperature. Further, Table 4 illustrates the electric conductivity at each temperature.

TABLE 4

| Concentration | Equation of electric conductivity-Temperature | Electric conductivity at 20° C. [mS/cm] | Electric conductivity at 25° C. [mS/cm] | Electric conductivity at 30° C. [mS/cm] |
|---|---|---|---|---|
| 1.189 | D = 0.0881T + 10.786 | 12.55 | 12.99 | 13.43 |
| 1.073 | D = 0.0807T + 9.857 | 11.47 | 11.87 | 12.28 |
| 1.009 | D = 0.0767T + 9.342 | 10.88 | 11.26 | 11.64 |
| 0.910 | D = 0.0705T + 8.547 | 9.957 | 10.31 | 10.66 |
| 0.806 | D = 0.0636T + 7.721 | 8.993 | 9.311 | 9.629 |

Then, an approximate straight line is derived with respect to a relationship between the concentration and electric conductivity of the aqueous solution of hydrofluoric acid at each temperature using the least squares method. Table 5 lists the approximate straight equation at each temperature.

TABLE 5

| Temperature [° C.] | Equation of electric conductivity-concentration | Distinction among inclinations | Distinction among intercepts |
|---|---|---|---|
| 20 | D = 9.921C + 1.634 | 0.319 | 0.062 |
| 25 | D = 9.602C + 1.572 | 0.319 | 0.062 |
| 30 | D = 9.283C + 1.510 | | |

It is found from Table 5 that distinctions among inclinations and distinctions among intercepts among the approximate lines are equal to each other. Accordingly, as illustrated in Table 6, the inclination w and the intercept z can be expressed as a linear function depending upon temperature T. Thus, the constants A, B, a, b in w=AT+B and z=aT+b are determined, and hence the constants of the equation (1) C=(D−aT−b)/(AT+B) are determined.

TABLE 6

| Inclination w | W = 0.0638T + 8.008 |
| Intercept z | Z = −0.0123T + 1.263 |

An aqueous solution of 1.0% by mass of hydrofluoric acid is diluted and prepared at temperature of 20 to 30° C. using the equation obtained in the foregoing step: C=(D−0.0123T−1.2634)/(0.0638T+8.0078). The dilution and the preparation are, for example, performed as follows:

Firstly, in the diluting preparation apparatus illustrated in FIG. 1, an agent and water are mixed and stirred into a uniform aqueous solution. Then, the concentration in the aqueous solution is detected. The concentration obtained by the foregoing equation from the temperature and electric conductivity of the diluted and prepared aqueous solution is outputted to the system control instrument 9 that is the concentration adjusting means controlled by a computer program, and is compared with a previously set desired value (1.0% by mass) and an allowable error range (±0.1% by mass). If the outputted concentration falls within an allowable error range with respect to the desired value, then the aqueous solution is sent to the supply tank 7. In contrast, if the concentration is less than the desired value including the allowable error range, then an agent stock solution is supplied, while if it exceeds the desired value, then pure water is supplied for re-preparing. For the re-prepared aqueous solution the aforementioned steps are repeated until the concentration of the solution falls within the desired value involving the allowable error range. However, in the diluting and preparing step for the agent stock solution, the temperature of the agent solution is varied within the range of 20 to 30° C. The concentration of the resulting aqueous solution of hydrofluoric acid is 1.0% by mass (measured by a neutralization titration).

Comparative Example 1

An aqueous 2.380% by mass TMAH solution is adjusted at temperature of 20 to 30° C. as in example 1, except for employing an equation C=(DT−0.7747 (T−25.0)−3.654)/16.42 including temperature compensation in addition to the linear equation expressing a relationship between the concentration and electric conductivity of the aqueous solution of TMAH at 25° C. as the equation for deriving the concentration of the agent solution during the dilution and preparation from the electric conductivity. Although in the diluting and preparing step for the agent stock solution the temperature of the agent solution is varied within the range of 20 to 30° C., the calculated concentration of the resulting aqueous solution of TMAH differs in maximum 0.0005% by mass from the concentration obtained within the above-mentioned temperature range (measured by a neutralization titration), causing the possibility of erroneous information being outputted at the minimum and maximum concentrations within the allowable error range.

Comparative Example 2

An aqueous solution of 1.0% by mass of hydrofluoric acid is prepared at the temperature of 20 to 30° C. as in the example 2, except for employing an equation C=(DT−0.0767(T−25.0)−1.572)/9.602 including temperature compensation in addition to the linear equation expressing the relationship between the electric conductivity and concentration of the aqueous solution of hydrofluoric acid at 25° C. as the equation for calculating the concentration of the agent during dilution and preparation from the electric conductivity. Although in the diluting and preparing step for the agent stock solution the temperature of the agent solution varies from 20 to 30° C., the calculated concentration of the resulting aqueous hydrofluoric acid solution differs in maximum 0.03% by mass from the concentration obtained within the above-mentioned temperature range (measured by neutralization titration), to cause the possibility of erroneous information being outputted at the minimum and maximum concentrations within the allowable error range.

In the present invention, the electric conductivity of a solution can be measured and the concentration of the solution can be detected without keeping the temperature of the solution at setting temperature in real time and with reduced variations of numerical values with a higher accuracy than the prior art. Accordingly, the present invention is preferably used in agent supply makers who dilute and prepare agents required for strict concentration control, and fields of semiconductor and liquid crystals for example where agent stock solutions are diluted and prepared for use. Since, upon measurement of the electric conductivity of a solution, it is unnecessary to keep the temperature of a solution at a setting temperature, there is eliminated the need of installation investment such as a temperature controller, etc., and the need of a heat source for temperature keeping apparatus, etc., and further the cost of diluting and preparing an agent can be reduced and diluting and preparing work for agents can be simplified. Furthermore, diluting and preparing for an agent is ensured in a narrow space.

The invention has been described with particular emphasis on the preferred embodiments, but variations and modifications within the spirit and scope of the invention may occur to those skilled in the art to which the invention pertains.

What is claimed is:

1. A method for detecting a concentration of a solution comprising:
   measuring an electrical conductivity and a temperature of a solution; and
   calculating a concentration of a desired substance in the solution, wherein the calculation of the concentration is achieved on the basis of the following formula:

$$C=(D-aT-b)/AT+B$$

wherein C is the concentration of a desired substance, D is the electrical conductivity of the solution at the temperature T, T is the temperature of the solution, and A, B, a, and b indicate constants.

2. The method for detecting a concentration of claim 1, wherein the constants A, B, a, and b in the formula are values which are obtained by measuring the electrical conductivities at a plurality of temperatures for each of the solutions containing the same desired substances with a plurality of concentrations and estimating the values with the least squares method.

3. The method for detecting a concentration of claim 1, wherein the constants A, B, a, and b are values estimated by a method including:
   a first step for measuring an electrical conductivity at a plurality of temperatures for each of the solutions containing the same agents with a plurality of concentrations;
   a second step for deriving a linear equation using the least squares method for a relationship between the temperature and the electrical conductivity at each concentration;
   a third step for calculating the electrical conductivity at each temperature by substituting the plurality of the temperatures for each of said linear equation;
   a fourth step for deriving a second linear equation with the least squares method with respect to the electrical conductivity and the concentration at each temperature in the third step; and
   a fifth step for deriving linear equations, w=AT+B and z=aT+b, depending upon temperature with respect to each of the inclination w and the intercept z of each second linear equation obtained in the fourth step.

4. The method for detecting a concentration of claim 1, wherein the plurality of the temperatures is included in a temperature range of ±5 degrees of a predetermined temperature.

5. The method for detecting a concentration of claim 1, wherein the plurality of the temperatures are included in the temperature range of ±10 degree of a predetermined temperature.

6. The method for detecting a concentration of claim 1, wherein the solution is an aqueous solution.

7. The method for detecting a concentration of claim 1, wherein the solution contains only one kind of a solute.

8. A method for preparing an agent to a desired concentration utilizing the following steps:
   measuring an electrical conductivity and a temperature of a solution;
   calculating a concentration of a desired substance in the solution, wherein the calculation of the concentration is achieved on the basis of the following formula:

$$C=(D-aT-b)/AT+B$$

wherein C is the concentration of a desired substance, D is the electrical conductivity of the solution at the temperature T, T is the temperature of the solution, and A, B, a, and b indicate constants; and
   diluting the substance to prepare the agent of the predetermined concentration.

9. The method for preparing an agent of claim 8, further comprising:
   a first step for mixing the agent with water into an aqueous solution thereof;
   a second step for detecting a concentration of the agent in the aqueous solution; and
   a third step for adding an agent or water into the aqueous solution to adjust the concentration of the agent to a predetermined concentration based upon the detected concentration of the agent.

10. The method for preparing an agent of claim 9, wherein at least the second step and the third step are controlled with a computer program.

* * * * *